(12) United States Patent
Nissl et al.

(10) Patent No.: US 7,942,921 B2
(45) Date of Patent: May 17, 2011

(54) REMOVABLE STENT

(75) Inventors: Thomas Nissl, Winsen (DE); Eric K. Mangiardi, Charlotte, NC (US)

(73) Assignee: Merit Medical Systems, Inc., South Jordan, UT (US)

( * ) Notice: Subject to any disclaimer, the term of this patent is extended or adjusted under 35 U.S.C. 154(b) by 608 days.

(21) Appl. No.: 10/573,948

(22) PCT Filed: Sep. 29, 2004

(86) PCT No.: PCT/US2004/031886
§ 371 (c)(1), (2), (4) Date: May 1, 2007

(87) PCT Pub. No.: WO2005/032411
PCT Pub. Date: Apr. 14, 2005

(65) Prior Publication Data
US 2007/0233230 A1    Oct. 4, 2007

(51) Int. Cl.
*A61F 2/06* (2006.01)
*A61F 2/90* (2006.01)
(52) U.S. Cl. .................. 623/1.15; 623/1.16; 606/198
(58) Field of Classification Search ........ 623/1.11–1.13, 623/1.15–1.16; 606/191, 194, 198
See application file for complete search history.

(56) References Cited

U.S. PATENT DOCUMENTS

| | | | |
|---|---|---|---|
| 5,035,706 A * | 7/1991 | Giantureo et al. | 606/198 |
| 5,156,609 A | 10/1992 | Nakao et al. | |
| 5,507,771 A * | 4/1996 | Gianturco | 606/198 |
| 5,749,921 A | 5/1998 | Lenker et al. | |
| 5,776,186 A | 7/1998 | Uflacker | |
| 5,897,589 A | 4/1999 | Cottenceau et al. | |
| 5,941,895 A | 8/1999 | Myler et al. | |
| 6,090,129 A | 7/2000 | Ouchi | |
| 6,165,209 A | 12/2000 | Patterson et al. | |
| 6,187,016 B1 | 2/2001 | Hedges et al. | |
| 6,241,757 B1 | 6/2001 | An et al. | |
| 6,361,540 B1 | 3/2002 | Gauderer et al. | |
| 6,375,676 B1 * | 4/2002 | Cox | 623/1.16 |
| 6,607,539 B1 | 8/2003 | Hayashi et al. | |

(Continued)

FOREIGN PATENT DOCUMENTS

DE            10335948 B3    2/2005

(Continued)

OTHER PUBLICATIONS

International Search Report for PCT/US2004/031886 completed Feb. 7, 2005.

(Continued)

*Primary Examiner* — David H Willse
*Assistant Examiner* — Tiffany Shipmon
(74) *Attorney, Agent, or Firm* — Stoel Rives LLP

(57) ABSTRACT

The invention is relative to a stent with a tubular support frame consisting of axially successively following, interconnected annular segments, which support frame is surrounded on its outside by a thread. The thread ends are guided via a deflection from the outside into support frame, where they are coupled by a connector consisting of a material visible in x-rays. Deflection is realized by two deflection elements in the form of eyelets provided on annular segment. Deflection elements are arranged on the circumference of support frame at an interval from one another and are provided on end-side annular segment, viewed in longitudinal direction L of the stent.

14 Claims, 4 Drawing Sheets

U.S. PATENT DOCUMENTS

| | | | |
|---|---|---|---|
| 6,676,692 B2 | 1/2004 | Rabkin et al. | |
| 6,679,893 B1 | 1/2004 | Tran | |
| 6,699,277 B1 | 3/2004 | Freidberg et al. | |
| 6,802,846 B2 | 10/2004 | Hauschild et al. | |
| 6,821,291 B2 | 11/2004 | Bolea et al. | |
| 7,175,652 B2 | 2/2007 | Cook et al. | |
| 7,252,680 B2 | 8/2007 | Freitag | |
| 2002/0040236 A1 | 4/2002 | Lau et al. | |
| 2002/0058986 A1* | 5/2002 | Landau et al. | 623/1.13 |
| 2002/0143387 A1 | 10/2002 | Soetikno et al. | |
| 2002/0188344 A1* | 12/2002 | Bolea et al. | 623/1.11 |
| 2003/0149475 A1 | 8/2003 | Hyodoh et al. | |
| 2004/0049262 A1* | 3/2004 | Obermiller et al. | 623/1.15 |
| 2004/0116996 A1 | 6/2004 | Freitag | |
| 2005/0119722 A1* | 6/2005 | Styrc et al. | 623/1.12 |
| 2007/0233230 A1 | 10/2007 | Nissl et al. | |
| 2007/0276463 A1 | 11/2007 | Nissl et al. | |
| 2008/0033528 A1 | 2/2008 | Satasiya et al. | |
| 2008/0140181 A1 | 6/2008 | Reynolds et al. | |

FOREIGN PATENT DOCUMENTS

| | | |
|---|---|---|
| EP | 0701800 A1 | 3/1996 |
| EP | 0857471 | 8/1998 |
| EP | 1308138 A2 | 5/2003 |
| JP | 11-057022 | 3/1999 |
| WO | WO-02/083037 A1 | 10/2002 |
| WO | WO-03/022181 A1 | 3/2003 |
| WO | WO 03/096935 | 11/2003 |
| WO | WO 2005/079705 | 9/2005 |

OTHER PUBLICATIONS

The Supplementary European Search Report for EP 04 78 9198, completed Apr. 25, 2007, mailed on May 4, 2007.
The Examination Report for EP 04 789 198.1, completed Oct. 25, 2007.
Advisory Action issued in U.S. Appl. No. 11/496,910 dated Oct. 18, 2009.
Examination Report for EP 04789198 dated Oct. 25, 2007.
International Search Report for PCT/US2005/038519 dated Feb. 22, 2006.
Office Action issued in U.S. Appl. No. 11/496,910 dated Oct. 15, 2009.
Office Action issued in U.S. Appl. No. 11/496,910 dated Mar. 18, 2009.
Restriction Requirement issued in U.S. Appl. No. 11/496,910 dated Feb. 3, 2009.
Office Action dated Jun. 24, 2010 for U.S. Appl. No. 11/577,859.
Office Action dated Jun. 10, 2010 for U.S. Appl. No. 11/496,910.
Office Action dated Dec. 14, 2010 for U.S. Appl. No. 11/496,910.
Office action dated Jan. 7, 2011 for U.S. Appl. No. 11/577,859.

* cited by examiner

REMOVABLE STENT

FIELD OF INVENTION

The invention is relative to a stent with suture mediated removability features.

BACKGROUND OF THE INVENTION

Stents are used to treat stenoses. Stenoses are closures and constrictions of tubular body canals acquired congenitally or conditioned by disease. Tumors that press on the body canals or deposits that close the body canals are frequently causes for stenoses. Stenoses can be opened by operative and non-operative measures. In the case of non-operative measures, stents are introduced by catheter techniques or introducing aids into the intracorporal vessel in the area of the stenosis. Stents function as prosthesis for supporting the inner walls of a lumen.

In various areas of application, e.g., bronchus, bilary, trachea or esophagus the stents must be able to removed out of the body as a function of the course of the disease or treatment. This can be problematic since newly formed tissue can grow on the support frame and even grow through it, which can result in complications when removing a stent.

In this connection a stent taught by DE 101 18 944 A1 belongs to the state of the art whose support frame is surrounded on the outside by a thread or wire. The support frame can be radially constricted by pulling on the thread ends, that are each provided with a loop or the like, which makes it possible for the frame to be removed. In particular when the wire or thread is guided or braided in multiple windings around the support frame, a high degree of friction results between the two stent components, which has a disadvantageous effect on the explantation process. Even the grasping of the thread ends can be complex at times.

SUMMARY OF EXEMPLARY EMBODIMENTS

The invention solves this problem in a stent in accordance with the features of protective Claim 1 in which the support frame is formed by several axially successive annular segments and in which at least two adjacent annular segments can be connected by positively intermeshing coupling elements.

The stent in accordance with the invention and the annular segments used to build the stent are constructed in a modular building-block system and can be individually composed. The stent can be used wherever different lengths and/or different properties, e.g., different degrees of radial forces or different geometries should be used or must be used.

A stent can be constructed or composed of individual annular segments or of annular segments combined in groups adapted to the particular requirements of use of the stenosis to be treated. A rapid reaction time for specific and specially adapted stents for a patient is possible.

The stent of the invention is adapted functionally by means of the combination of annular segments with different properties, in particular with radial forces that differ from each other. This can take place by the combination of annular segments with a differing design and/or consisting of different materials.

The suggested stent also has manufacturing and economical advantages. Thus, the rejection rate can be reduced by using short, individual annular segments. An individual annular segment is, e.g., 20 mm long. A complete stent can then be composed of 6 individual annular segments with a total length of 120 mm. If an annular segment is defective, only this single short annular segment needs to be replaced, whereas, in the case of a support frame with a one-piece construction the entire stent would be unusable.

The connection of the annular segments via the coupling elements is positive, but articulated in a limited manner. This measure is advantageous for the direction of the curves of the stent.

The annular segments are connected via positively intermeshing coupling elements. The coupling elements are preferably designed as complementary claw connectors, as provided in protective Claim 2. It is advantageous if both coupling elements project axially relative to the annular segments in the direction of the longitudinal axis of the stent (protective Claim 3). However, it is also conceivable that one of the coupling elements is designed inside the annular segment so that only one corresponding coupling element projects in the axial direction of the stent. It can be advantageous in practice to use special terminal annular segments on the free ends of a stent of the invention which segments comprise coupling elements only on one side in the direction of the middle of the stent.

The annular segments are positively connected by the coupling elements. To this end the coupling elements have undercut areas for producing a stable connection. The undercut areas can be curved (protective Claim 4). Straight-line undercut areas are also advantageous (protective Claim 5). In addition, a combination of curved undercut areas and of straight-line undercut areas on the coupling elements is also possible. The coupling elements are supported on each other by the undercut areas so that a reliable, positive coupling of the annular segments among themselves is assured.

A number of annular segments can be advantageously interlocked to stent sections by connector struts, as provided in protective Claim 6. According to this claim a number of annular segments are firmly connected by connector struts. The individual sections again comprise coupling elements that make possible a positive connection of the annular segments or of the stent sections to each other in accordance with the invention.

According to the features of protective Claim 7 the annular segments are formed by corrugated struts that endlessly follow each other. All deformable, medically possible metals or metal alloys can be used in this instance, e.g., high-grade steel, cobalt alloys, technical pure iron or nickel-titanium alloys or other medical implant materials.

The invention is described in detail in the following using exemplary embodiments. Further objectives, features and advantages of the invention will be apparent from the following detailed description taken in conjunction with the accompanying drawings.

DETAILED DESCRIPTION OF AN EMBODIMENT

Figure 1:
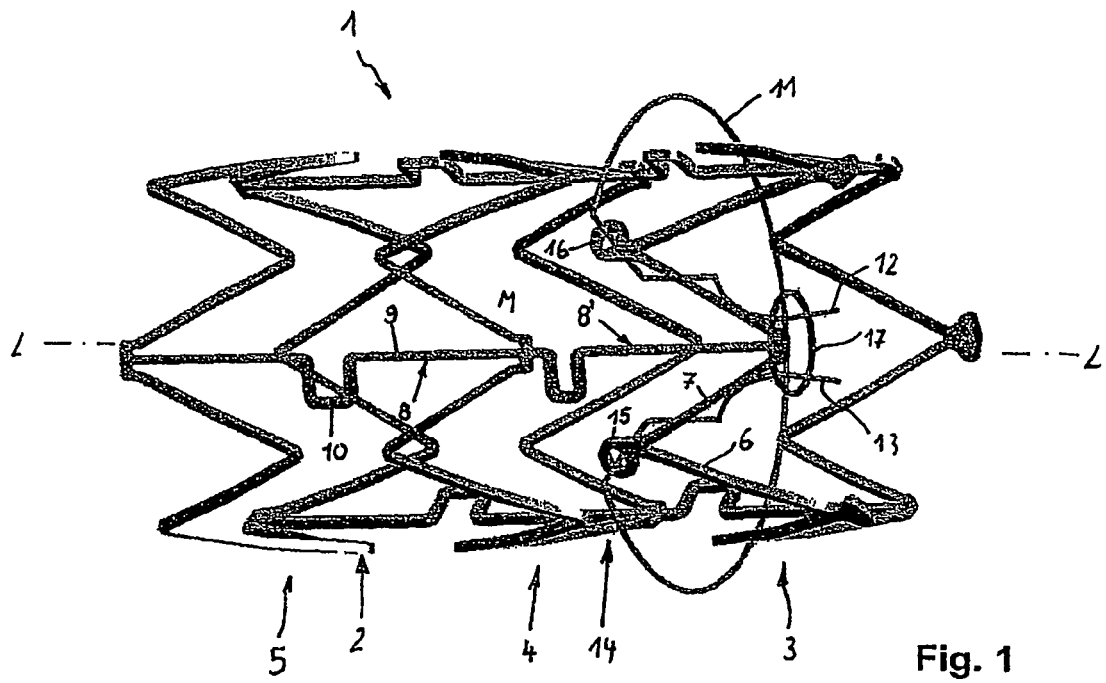
FIG. 1 shows the stent pattern of a stent in accordance with the invention in a developed view.

The invention is therefore based on the problem of creating a functionally improved, removable stent.

The invention solves this problem with a stent in accordance with the features of Claim 1.

The core of the invention is constituted by the measure that the support frame of the stent is surrounded on the outside by a thread and that the thread ends are guided via a deflection from the outside into the support frame where they are coupled by a connector.

In this manner the friction is distinctly reduced in contrast to a threaded thread, which substantially improves the explantation process of a stent. The ends coupled in the interior of the support frame by the connection can be readily grasped with a suitable instrument. If the edges of the stent should be granulated or grown in, the support frame can be drawn together, preferably partially in the area of the first annular segment, by pulling the thread. The stent constricted in this manner can then be removed from the body canal.

A biocompatible, non-dissolvable thread can be used as thread. The term "thread" can also denote a wire.

The deflection for the thread ends can basically be realized by differently designed deflection elements. Eyelet-shaped, loop-shaped or hook-like deflection elements are considered to be especially advantageous. The deflection elements should reliably hold and guide the thread.

According to the features of Claim 2 the deflection is realized by at least one deflection element provided on an annular segment.

The deflection is preferably formed by two deflection elements, e.g., eyelets, arranged on the circumference of the support frame at an interval from one another (Claim 3).

The explanation process can already be distinctly simplified if one or two end-side annular segments of a stent can be drawn together. The features of Claim 4 consequently provide that the deflection is provided on the end-side annular segment (viewed in the direction of the longitudinal axis of the stent).

Another advantageous embodiment of the stent of the invention provides according to Claim 5 that the deflection is arranged on the inner side, facing the middle of the stent, of the end-side annular segment.

An alternative embodiment forms subject matter of Claim 6. According to it the deflection is formed by two deflection elements of which a first deflection element is arranged on the inner side, facing the middle of the stent, of an annular segment and the second deflection element is arranged on the outer side of the annular segment. Accordingly, the two deflection elements are spaced relative to one another over the circumference of the support frame as well as viewed in the direction of the longitudinal axis of the stent. An entire annular segment is drawn together when the thread ends are pulled by the diagonal course of the thread achieved in this manner via the annular segment and the connector struts.

Furthermore, the deflection can also be formed by two deflection elements of which a first deflection element is provided on the end-side annular segment, viewed in the direction of the longitudinal axis of the stent, and the second deflection element is provided on the adjacent, inner annular segment (Claim 7).

According to the features of Claim 8 the connector consists of a material visible in x-rays. The coupling site on the thread ends can be detected by x-rays in this manner, which facilitates the medical intervention for explanting a stent.

In addition, other guide elements for the thread can be provided in the support frame in order to support the purposeful position of the yarn on the support frame, as is provided in Claim 9.

The annular segments themselves are formed by struts following each other in an endless manner in a corrugated manner. According to Claim 10 adjacent annular segments are coupled by connector struts. Each connector strut has a longitudinal section running substantially parallel to the longitudinal axis of the stent and has a strut section aligned transversely to the latter and configured in a U or V shape (Claim 11).

This embodiment of the support frame assures a high and anatomically flexible support force and is stable in length even given external compression.

The invention is described in detail in the following with reference made to the exemplary embodiments shown in the drawings.

FIG. 1 shows a three-dimensional view of a stent in accordance with the invention.

FIGS. 2 to 5 and 7 each show a section of a stent with the representation of five different configurations of the support frame.

Figure 6:
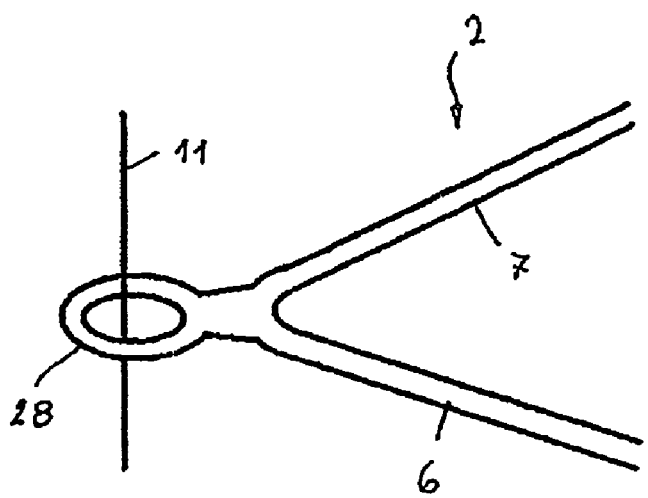
FIG. 6 shows a section from the stent pattern of another embodiment of a stent.

FIG. 6 shows a section of the support frame with the representation of a guide eyelet. In all figures components corresponding to each other have the same reference numerals.

FIG. 1 shows a stent in accordance with the invention in a three-dimensional representation.

Stent 1 comprises a tubular support frame 2 on axially sequential, interconnected annular segments 3, 4, 5. Each annular segment 3, 4, 5 is formed by struts 6, 7 following each other in an endless manner in a corrugated or zigzag pattern. Adjacent annular segments 3, 4 and 4, 5 are coupled by connector struts 8. Connector struts 8 have a longitudinal section 9 running substantially parallel to longitudinal axis L of the stent and have a strut section 10 aligned transversely to the latter and configured in a U or V shape (refer also to FIG. 2 in this regard).

The illustration according to FIG. 1 shows stent 1 in its widened out supporting state.

Support frame 2 is surrounded on the outside by thread 11. For the sake of a better understanding thread 11 is shown in FIG. 1 at an interval from support frame 2. Thread 11 surrounds support frame 2 in an annular fashion between annular segments 3, 4. The two thread ends 12, 13 of thread 11 are guided into the interior of support frame 2 via deflection 14 in the form of two deflection elements 15, 16 formed by eyelets. Thread ends 12, 13 are firmly connected to one another by connector 17 consisting of a material visible to x-rays. FIG. 1 shows connector 17 in a simplified manner. Connector 17 couples the two thread ends 12, 13 firmly and quasi inseparably to one another.

Figure 2:
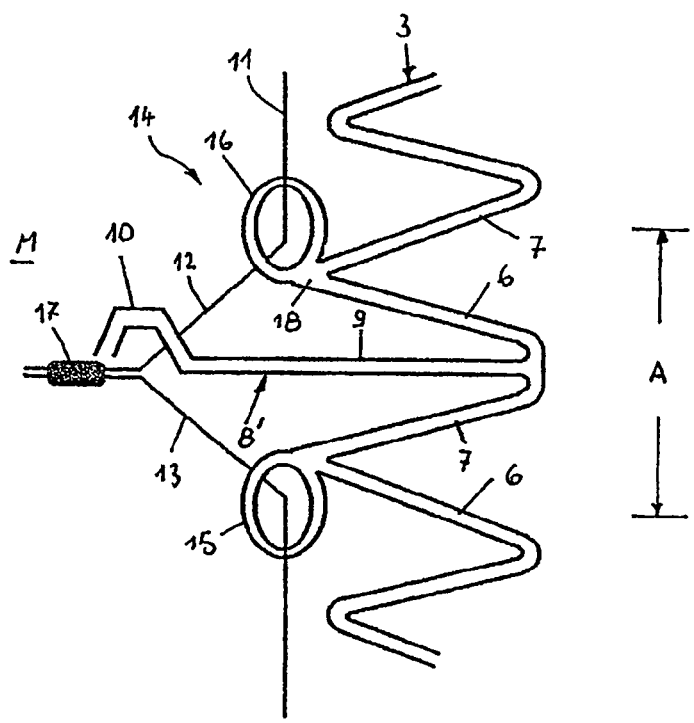
FIG. 2 shows a section of the stent pattern according to FIG. 1.

FIG. 2 shows a section of support frame 2 corresponding to FIG. 1. Deflection 14 is provided on end-side (viewed in the direction of longitudinal axis L of the stent) annular segment 3. The two deflection elements 15, 16 are arranged on the inner side, facing the middle of the stent, of annular segment 3 and in transitional area 18 between two struts 6, 7. Deflection elements 15, 16 are located on the circumference of support frame 2 at distance A from one another.

Thread 11 runs between annular segments 3, 4 and loops around connector struts 8 with the exception of connector strut 8' between the two deflection elements 15, 16.

In order to remove an implanted strut 1 from a body canal thread 11 is grasped in the interior of support frame 2 on connector 17. The two annular segments 3, 4 are drawn together via connector struts 8 by the traction applied from the outside and are reduced in diameter. Stent 1 can subsequently be removed without problems.

Figure 7:
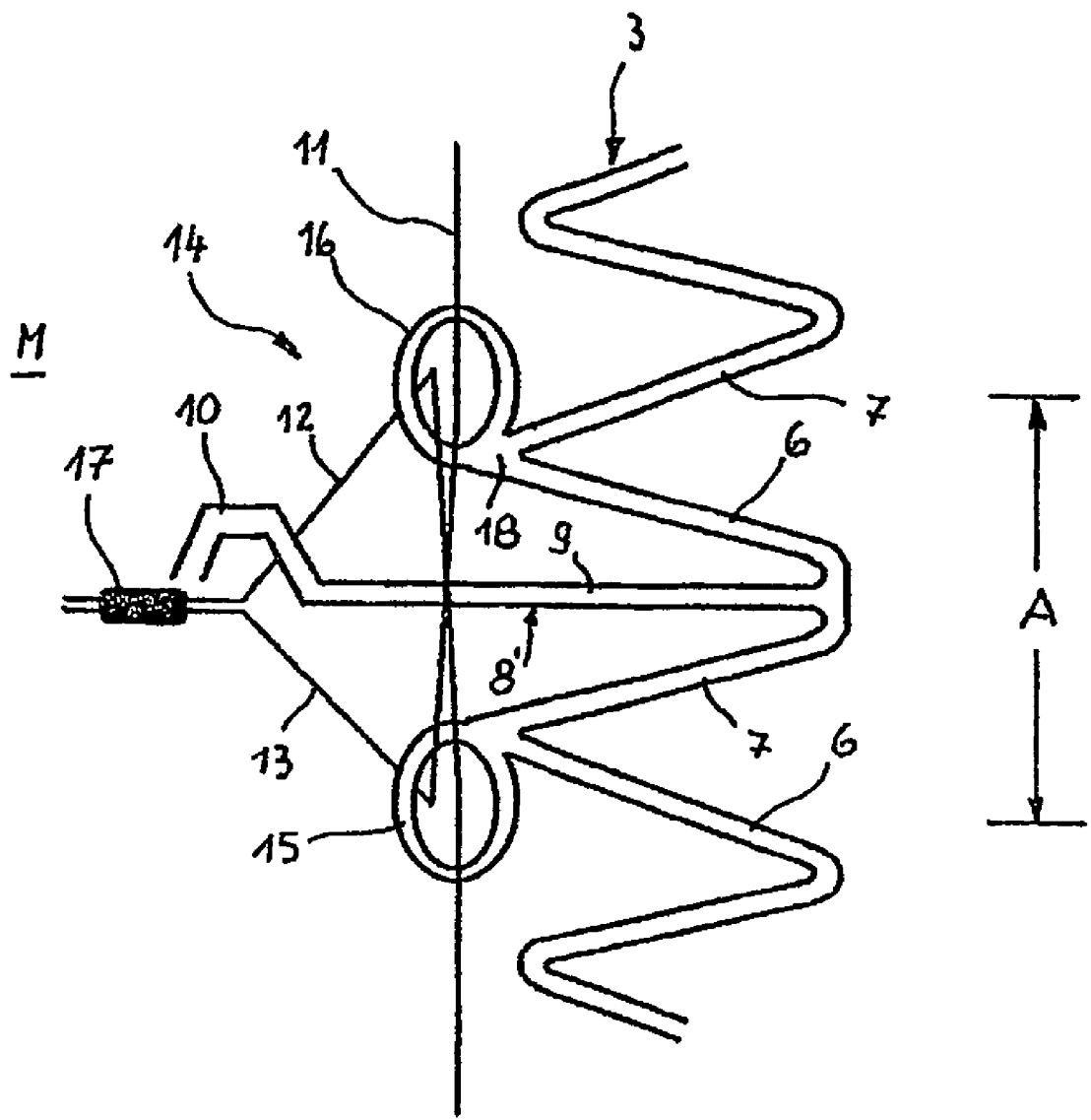
FIG. 7 shows the coupling elements of the stent according to FIG. 6, also on an enlarged scale.

Thread 11 can also overlap or cross itself on the end side before thread ends 12, 13 are guided via deflection elements 15, 16 of deflection 14 into the interior of support frame 2. Such a situation is shown in FIG. 7. Otherwise, the construction of the stent corresponds to the one previously described using FIGS. 1, 2. In this configuration struts 6, 7 are drawn onto connector 8' with deflection elements 15, 16 and all connectors 8, 8' and annular segments 3, 4 are radially constricted therewith by traction on thread ends 12, 13 via thread 11.

Figure 3:
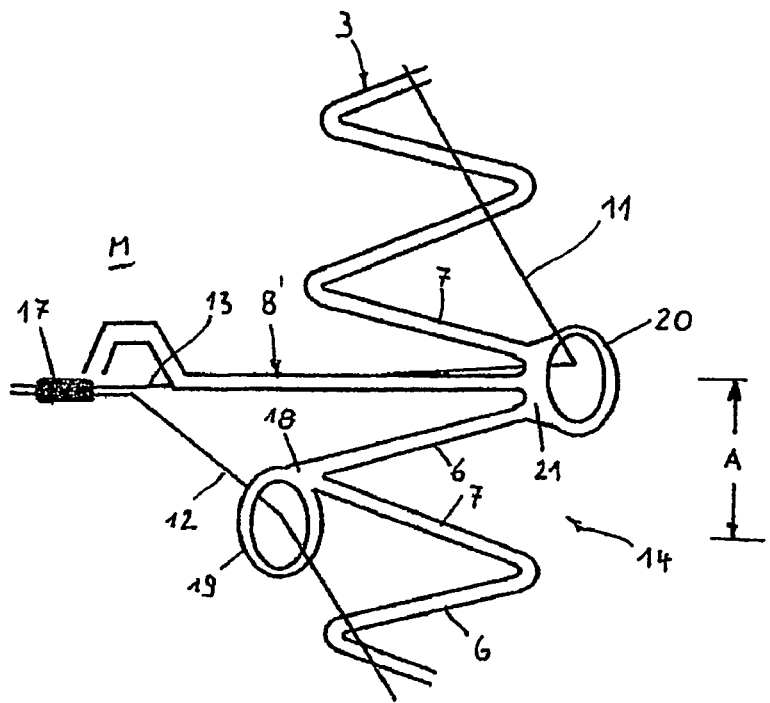
FIG. 3 shows the coupling elements of the stent according to FIGS. 1 and 2 on an enlarged scale.

In the embodiment of a support frame 2 according to FIG. 3 deflection 14 is formed by two deflection elements 19, 20 in the form of eyelets of which a first deflection element 19 is arranged on the inner side, facing the middle of the stent, of annular segment 3 and the second deflection element 20 is arranged on the outer side of annular segment 3. The first deflection element 19 is located in transitional area 18 between struts 6, 7 and in contrast thereto second deflection element 20 is arranged in transitional area 21 between struts 6, 7 and connector strut 8 on the side facing away from connector strut 8.

Thread 11 looping around support frame 2 on its outside is again guided via deflection 14 into support frame 2. To this end thread ends 12, 13 of thread 11 are threaded through deflection elements 19, 20 and coupled in support frame 2 by connector 17. As a consequence of the diagonal course of thread 11 via annular segment 3 achieved in this configuration, this second end is totally constricted during the drawing together by thread 11.

Figure 4:
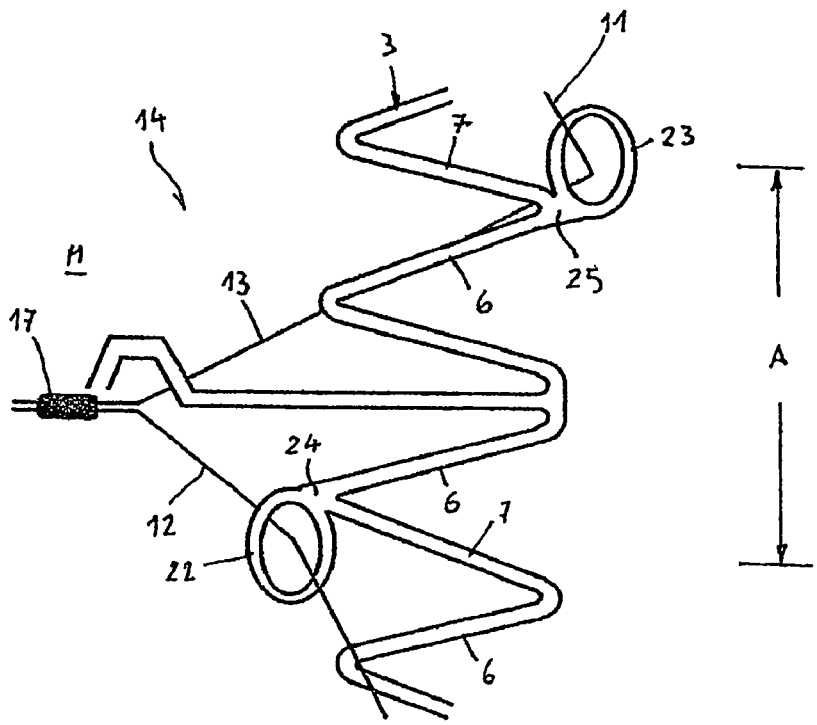
FIG. 4 shows a section from the stent pattern of another embodiment of a stent.

FIG. 4 shows a comparable configuration. It also has a first deflection element 22 in the form of an eyelet arranged on the inner side, facing middle M of the stent, of annular segment 3 and has a second deflection element 23 on the outer side of annular segment 3. First deflection element 22 is located on transitional area 24 between struts 6, 7 of the inner side of annular segment 3 and second deflection element 23 is located on transitional area 25 between struts 6, 7 on the outer side of annular segment 3. Interval A between deflection elements 22, 23 is greater over the circumference than that in the embodiment of support frame 2 according to FIG. 3.

Here too, a diagonal thread course is achieved on the outside of support frame 2 via struts 6, 7 and connector struts 8 so that when thread 11 is pulled the entire annular segment 3 is contracted.

Figure 5:
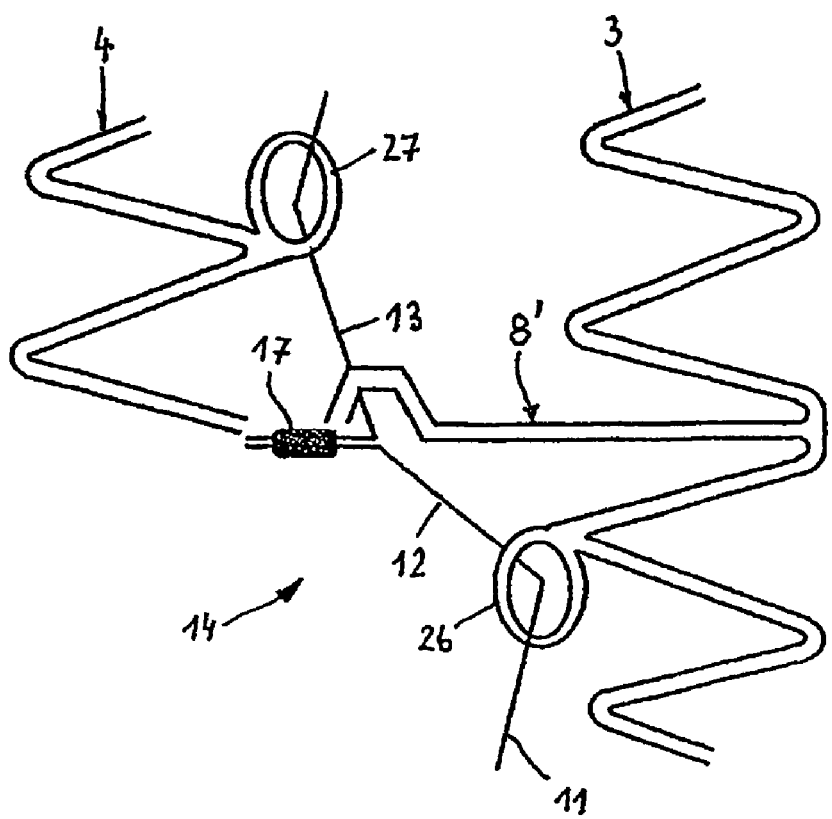
FIG. 5 shows the coupling elements of the stent according to FIG. 4 on an enlarged scale.

In the case of a stent 1 with a support frame 2 according to FIG. 5 deflection 14 is formed by two deflection elements 26, 27 of which the first deflection element 26 is provided on the end-side annular segment 3, viewed in longitudinal axis L of the stent and the second deflection element 27 is provided on adjacent, inner annular segment 4. In this instance too deflection elements 26, 27 are preferably formed by eyelets. According to the invention thread 11 is guided via deflection elements 26, 27 from the outside into the interior of support frame 2, where it is coupled by connector 17. Both annular segments 3, 4 are contracted when thread 11 is pulled as a result of the connecting of deflection elements 26, 27 to the first, inner segment area and to the second, outer segment area of annular segments 3, 4, whereupon stent 1 can be removed from the body canal.

LIST OF REFERENCE NUMERALS

1—stent
2—support frame
3—annular segment
4—annular segment
5—annular segment
6—strut
7—strut
8—connector strut
8'—connector strut
9—longitudinal section
10—strut section
11—thread
12—thread end
13—thread end
14—deflection
15—deflection element
16—deflection element
17—connector
18—transitional area
19—deflection element
20—deflection element
21—transitional area
22—deflection element
23—deflection element
24—transitional area
25—transitional area
26—deflection element
27—deflection element
28—guide element
L—longitudinal axis of stent
A—interval
M—middle of stent The present invention may be embodied in other specific forms without departing from its spirit or essential characteristics. The described embodiments are to be considered in all respects only as illustrative, and not restrictive. The scope of the invention is, therefore, indicated by the appended claims, rather than by the foregoing description. All changes, which come within the meaning and range of equivalency of the claims, are to be embraced within their scope.

What is claimed is:

1. A removable stent comprising:
a plurality of annular segments arranged axially successively and interconnected to form a tubular support frame;
one or more deflection elements coupled to at least one of the plurality of annular segments and positioned on a circumference of the tubular support frame;
a thread at least partially encircling the tubular support frame outside of the circumference of the tubular support frame and positioned between annular segments, the thread having a first end and second end that are each guided by one of the one or more deflection elements from the outside of the tubular support frame into a position inside the tubular support frame;
a connector positioned inside the tubular support frame to securely couple together the first and second thread ends, wherein displacement of the connector relative to the stent along a longitudinal axis of the stent results in contraction of at least two of the plurality of annular segments.

2. The stent according to claim 1, wherein the first and second ends of the thread are guided by the same deflection element.

3. The stent according to claim 1, wherein the first end of the thread is guided by a first of the one or more deflection elements and the second end of the thread is guided by a second of the one or more deflection elements, wherein the first deflection element and second deflection element are positioned at an interval from one another.

4. The stent according to claim 1, wherein the one or more deflection elements are provided on an end-side annular segment, viewed in the direction of the longitudinal axis of the stent.

5. The stent according to claim 1, wherein the one or more deflection elements are positioned on an inner side, facing the middle of the stent, of the annular segment.

6. The stent according to claim 3, wherein the first deflection element is arranged on the inner side, facing the middle of the stent, of an annular segment and the second deflection element is arranged on the outer side of the annular segment.

7. The stent according to claim 3, wherein the first deflection element is provided on an end-side annular segment, viewed in the direction of the longitudinal axis of the stent, and the second deflection element is provided on an adjacent annular segment.

8. The stent according to claim 1, wherein the connector comprises a material visible in x-rays.

9. The stent according to claim 1, further comprising additional guide elements coupled to the tubular support frame.

10. The stent according to claim 1, wherein the plurality of annular segments are formed by struts that follow one another in an endless, corrugated manner, and wherein adjacent annular segments are coupled by connector struts.

11. The stent according to claim 10, wherein each connector strut comprises a longitudinal section running substantially parallel to the longitudinal axis of the stent and comprises a strut section aligned transversely to the connector strut and configured in one of a U shape and a V shape.

12. A removable stent comprising:
a plurality of annular segments arranged axially successively and interconnected to form a tubular support frame;
one or more deflection elements coupled to at least one of the plurality of annular segments and positioned on a circumference of the tubular support frame;
a thread encircling the tubular support frame outside of the circumference of the tubular support frame, the thread having a first end and second end that are each guided by one of the one or more deflection elements from the outside of the tubular support frame into a position inside the tubular support frame;
a connector positioned inside the tubular support frame to fixedly couple together the first and second thread ends, wherein the connector is formed of a material distinct from the thread and displacement of the connector relative to the stent along a longitudinal axis of the stent results in contraction of at least two of the plurality of annular segments.

13. The stent according to claim 12, wherein the thread is positioned between annular segments.

14. The stent according to claim 12, wherein the connector comprises a material visible in x-rays.

* * * * *